United States Patent
Lee

(10) Patent No.: US 9,943,263 B2
(45) Date of Patent: Apr. 17, 2018

(54) WRIST WATCH STYLE BLOOD PRESSURE MONITOR

(71) Applicant: Dong Hwa Lee, Yongin-si (KR)

(72) Inventor: Dong Hwa Lee, Yongin-si (KR)

(73) Assignee: Charm Care Co., Ltd., Seoul (KR)

( * ) Notice: Subject to any disclaimer, the term of this patent is extended or adjusted under 35 U.S.C. 154(b) by 343 days.

(21) Appl. No.: 14/395,059

(22) PCT Filed: May 9, 2013

(86) PCT No.: PCT/KR2013/004050
§ 371 (c)(1),
(2) Date: Oct. 16, 2014

(87) PCT Pub. No.: WO2013/169014
PCT Pub. Date: Nov. 14, 2013

(65) Prior Publication Data
US 2015/0335282 A1    Nov. 26, 2015

(30) Foreign Application Priority Data

May 9, 2012 (KR) .................. 10-2012-0049196

(51) Int. Cl.
*A61B 5/02* (2006.01)
*A61B 5/00* (2006.01)
*A61B 5/022* (2006.01)

(52) U.S. Cl.
CPC ............ *A61B 5/681* (2013.01); *A61B 5/0004* (2013.01); *A61B 5/02233* (2013.01);
(Continued)

(58) Field of Classification Search
CPC ....... A61B 5/681; A61B 5/742; A61B 5/6898; A61B 5/02233; A61B 5/0004; A61B 5/0015; A61B 2562/0247
See application file for complete search history.

(56) References Cited

U.S. PATENT DOCUMENTS 3,101,863 A * 8/1963 Jackson, Sr. ............ F16K 13/04
                                              215/233
3,858,573 A * 1/1975 Ryan ...................... A61B 5/097
                                              128/205.12
(Continued)

FOREIGN PATENT DOCUMENTS

KR   10-2005-008421 A   1/2005
KR   10-2009-0001752 A  1/2009
(Continued)

OTHER PUBLICATIONS

English Machine Translation of KR 20090029556 A.*
(Continued)

*Primary Examiner* — Navin Natnithithadha
*Assistant Examiner* — Andrey Shostak
(74) *Attorney, Agent, or Firm* — Park, Kim & Suh, LLC

(57) ABSTRACT

A wrist watch style blood pressure monitor is configured to be mounted on a wrist of an examinee at ordinary times in order to measure and monitor blood pressure. The wrist watch style blood pressure monitor includes a blood pressure monitor main body which comprises a blood pressure display to display a blood pressure of the examinee. A band is coupled to the blood pressure display and is wound around the wrist of the examinee. An air chamber is provided at one side of the band and filled with air to compress a skin surface of the wrist. A pressure sensor is provided to measure the blood pressure from an aorta radialis when the air chamber compresses the aorta radialis.

11 Claims, 3 Drawing Sheets

(52) U.S. Cl.
CPC ............ *A61B 5/6898* (2013.01); *A61B 5/742* (2013.01); *A61B 5/0015* (2013.01); *A61B 2562/0247* (2013.01)

(56) References Cited

U.S. PATENT DOCUMENTS

| | | | | |
|---|---|---|---|---|
| 6,151,968 A | * | 11/2000 | Chou | A61B 5/681 |
| | | | | 73/748 |
| 6,336,901 B1 | * | 1/2002 | Itonaga | A61B 5/02141 |
| | | | | 600/499 |
| 6,491,647 B1 | * | 12/2002 | Bridger | A61B 5/021 |
| | | | | 128/900 |
| 2007/0197887 A1 | * | 8/2007 | Lunak | A61B 5/02055 |
| | | | | 600/323 |
| 2007/0287923 A1 | * | 12/2007 | Adkins | A61B 5/412 |
| | | | | 600/485 |
| 2008/0058620 A1 | * | 3/2008 | Lee | A61B 5/021 |
| | | | | 600/323 |

FOREIGN PATENT DOCUMENTS

| | | | |
|---|---|---|---|
| KR | 20090001752 A | * | 1/2009 |
| KR | 10-2009-0029556 A | | 3/2009 |
| KR | 20090029556 A | * | 3/2009 |
| KR | 10-2010-0005849 A | | 1/2010 |

OTHER PUBLICATIONS

English Machine Translation of KR 20090001752 A.*
International Search Report in International Application No. PCT/KR2013/004050, dated Aug. 27, 2013.

* cited by examiner

【Figure 1】
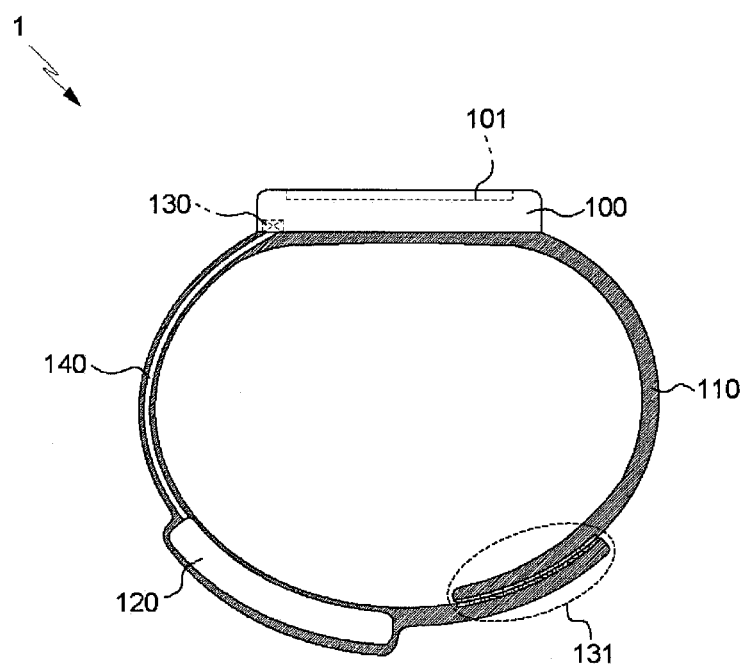
【Figure 2】
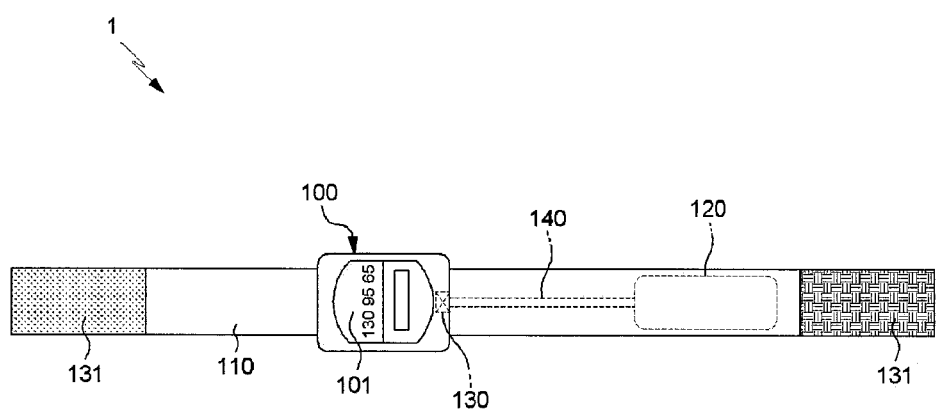

[Figure 3]
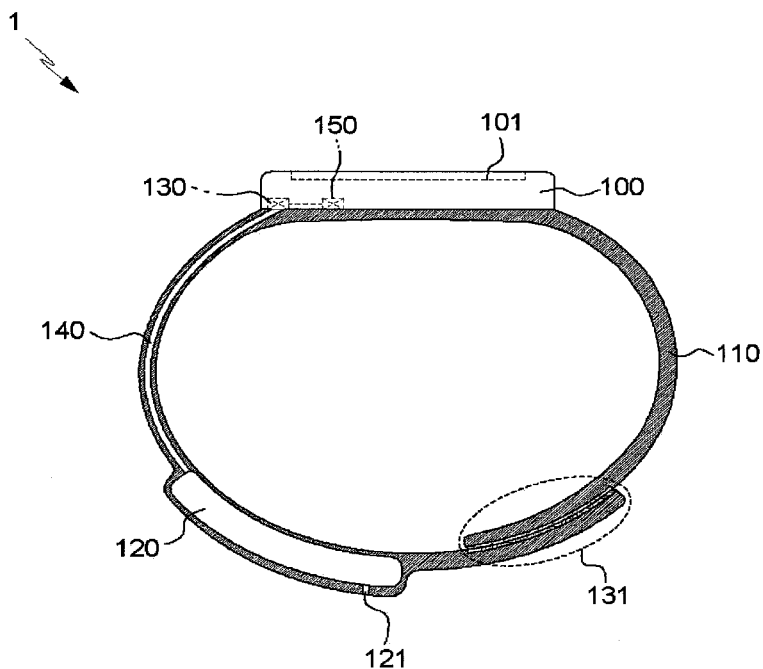
[Figure 4]
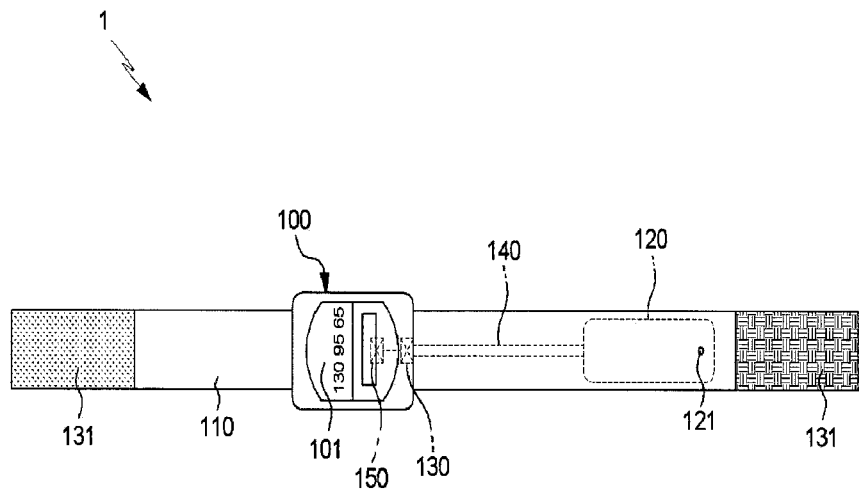

【Figure 5】
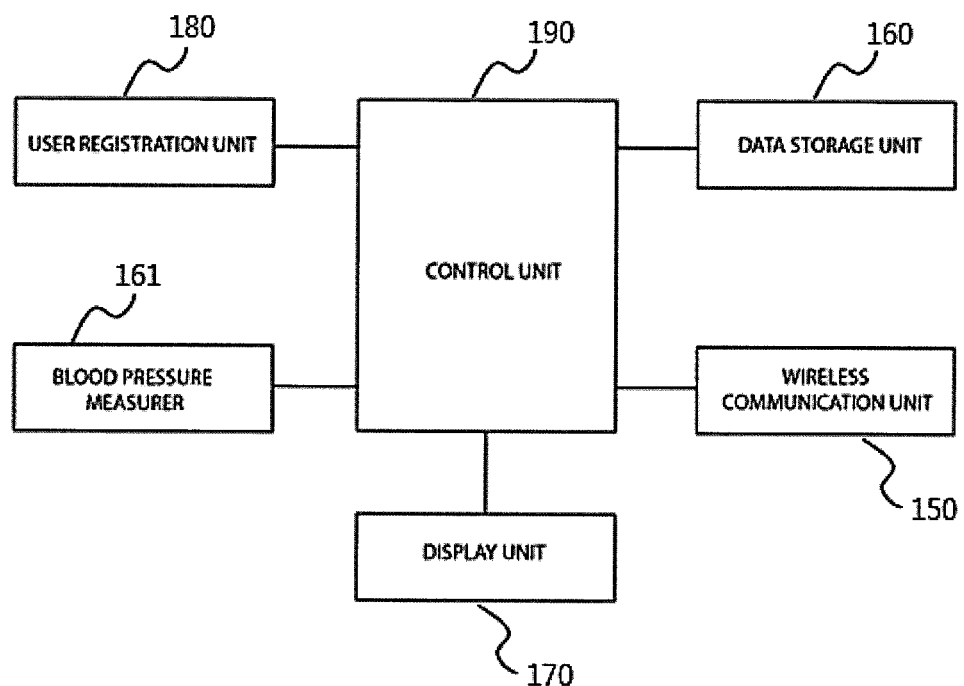

WRIST WATCH STYLE BLOOD PRESSURE MONITOR

CROSS-REFERENCE TO RELATED APPLICATIONS

This application is the National Stage filing under 35 U.S.C. 371 of International Application No. PCT/KR2013/004050, filed on May 9, 2013, which claims the benefit of Korean Patent Application No. 10-2012-0049196, filed on May 9, 2012, the contents of which are all hereby incorporated by reference herein in their entirety.

TECHNICAL FIELD

The present invention relates to a blood pressure monitor for checking blood pressure, and more particularly to a wrist wearable blood pressure monitor, i.e. a wrist watch style blood pressure monitor which is convenient to take blood pressure since it is portable being mounted to a wrist at ordinary times, and is capable of accurately measuring the blood pressure even though it has a simple structure.

BACKGROUND ART

In general, blood pressure refers to the pressure of blood against the wall of a blood vessel, and a heart alternates between contraction and relaxation about 60 to 80 times a minute. The pressure applied to the blood vessel when the heart contracts to push out blood is called 'systolic blood pressure' and also called 'maximal blood pressure' since the blood pressure is the highest. Further, the pressure maintained in the blood vessel when the heart is relaxed to receive blood is called 'diastolic blood pressure' and also called 'minimal blood pressure' since the blood pressure is the lowest.

Usually, a normal person has a systolic blood pressure of 120 mmHg and a diastolic blood pressure of 80 mmHg. In Korea, one or more in four adults have high blood pressure and this proportion rapidly increases after the age of 40.

The high blood pressure becomes a problem since it can lead to life-threatening complications such as eye diseases, renal diseases, artery diseases, brain diseases and heart diseases if the high blood pressure is left untreated. Therefore, the consistent measurement and management of the blood pressure are needed for a hypertensive patient who is at risk for the complications or has the complications.

With recent increased concern over health, various kinds of blood pressure measuring devices have been developed.

As a method of measuring the blood pressure, there are a Korotkoff sounds method, an oscillometric method, a tonometric method, etc.

The Korotkoff sounds method is a typical pressure measuring method, in which a body part where arterial blood flows is compressed enough to stop the flow of the blood and then the pressure at a moment when a pulse first sounds is taken as systolic pressure and the pressure at a moment when the pulse sound disappears is taken as diastolic pressure while the blood pressure is lowered.

The oscillometric method and the tonometric method are methods applicable to a digital blood pressure measuring device.

Like the Korotkoff sounds method, the oscillometric method sufficiently presses the body part where the arterial blood flows, so that the flow of the arterial blood can be stopped. Then, pulse waves, generated while the blood pressure is lowered at a constant speed or while the blood pressure of the body part is raised at a constant speed, are sensed, thereby taking the systolic pressure and the diastolic pressure.

In this method, pressure that has a constant level as compared with the maximum amplitude of the pulse wave may be taken as the systolic pressure or the diastolic pressure, or pressure of when the pulse wave amplitude is rapidly changed may be taken as the systolic pressure or the diastolic pressure.

Further, while the body part is compressed and then decompressed at a constant speed, the systolic pressure is measured earlier than the moment when the pulse wave has the maximum amplitude and the diastolic pressure is measured later than the moment when the pulse wave has the maximum amplitude. On the other hand, while the compression is increased at a constant speed, the systolic pressure is measured later than the moment when the pulse wave has the maximum amplitude and the diastolic pressure is measured earlier than the moment when the pulse wave has the maximum amplitude.

Next, the tonometric method refers to a method of successively measuring the blood pressure based on the amplitude and shape of a pulse wave generated when a body part is compressed not to completely stop the flow of the arterial blood.

As described above, a blood pressure monitor for measuring the blood pressure is the most basic medical device for taking the blood pressure as a basic health index, and is thus not only almost essentially provided in general clinics and hospitals but also well used at home, a sport center, etc. to measure personal blood pressure.

However, most of conventional blood pressure monitors have been produced as a forearm style that the blood pressure monitor is wound around an upper arm (or a portion from a shoulder to an elbow) and measures the blood pressure whenever there is a need of measuring the blood pressure. Accordingly, the blood pressure monitor is inconvenient to carry and is not easy to measure the blood pressure anytime a user wants.

For example, the existing blood pressure monitor based on the oscillometric method has been produced as only the forearm style, and thus needs a blood pressure monitor main body wound around and compressing a forearm, a pressure cuff, a tube plug, an air hose, etc. Therefore, a conventional blood pressure monitor has a complicated structure and is bulky. Further, it is cumbersome to use the conventional blood pressure monitor since there are many preparations for measurement, for instance, the air hose has to be fitted to face down for correct measurement, the cuff has to be mounted being higher than the elbow by 1-2 cm, and so on.

In particular, change in the blood pressure is varied depending on physical features of an examinee, and therefore a patient who has complications has to check his/her blood pressure periodically and/or directly when s/he feels sick. However, a mercury blood pressure monitor and an electronic blood pressure monitor are inconvenient for the patients due to the following problems.

First, the mercury blood pressure monitor and the electronic blood pressure monitor employ the cuff that requires air injection. However, the cuff is so bulky that it is cumbersome for a user to wear the cuff in real time.

In addition, the mercury blood pressure monitor employing a pneumatic cuff is so bulky and heavy that it is impracticable for an examinee (i.e. a patient), who has to frequently measure his/her blood pressure, to always carry.

Further, it is cumbersome to attach and detach the blood pressure monitor whenever there is a need of checking the blood pressure.

Although there has been proposed a pneumatic electronic blood pressure monitor having the same accuracy as the foregoing conventional blood pressure monitor, it is heavy and bulky since an electric pump and an air injection cuff are employed and thus causes a patient not to move freely if he or she has to carry the blood pressure monitor and periodically check his/her blood pressure.

Besides, there have been proposed pressureless electronic blood pressure monitors that measure the blood pressure based on pulses at a wrist or a fingertip and various parameters. However, such a pressureless electronic blood pressure monitor has low precision since it is difficult to correctly specify and universally offer the parameters, and is hardly applicable to patients who have to periodically and accurately check his/her blood pressure.

In addition, a blood pressure monitor mounted to a wrist and capable of measuring the blood pressure has recently been released under the name of wrist watch style blood pressure monitor.

However, the existing wrist watch style blood pressure monitor is not small enough in volume to be mounted to a wrist like a watch even though it is called the wrist watch style for no other reason but being mounted to the wrist for measuring the blood pressure.

That is, the conventional wrist watch style blood pressure monitor has been achieved by only reducing the size of the conventional blood pressure monitor so as to be applicable to a wrist instead of an upper arm since the blood pressure is measured in such a way of wearing a pressure cuff and operating a pump.

DISCLOSURE

Technical Problem

The present invention is conceived to solve the foregoing problems of the conventional blood pressure monitor, and it is an aspect of the present invention to provide a wrist wearable blood pressure monitor which is convenient to take blood pressure since it is mounted to a wrist at ordinary times and is capable of accurately measuring the blood pressure even though it has a simple structure without a cuff, a pump or the like.

In more detail, it is an aspect of the present invention to provide a portable blood pressure measuring device which can be mounted to a body part such as a wrist and measure blood pressure by an oscillometric method or a tonometric method without inconvenience in living a daily life, and transmit the blood pressure measurement through wireless communication so that the blood pressure can be efficiently managed.

Technical Solution

In accordance with one aspect of the present invention, a wrist watch style blood pressure monitor that can be mounted to a wrist of an examinee at ordinary times includes: a blood pressure monitor main body which includes a measured blood pressure display to display measured blood pressure of an examinee; a band which is coupled to the measured blood pressure display and wound around a wrist; an air chamber which is provided at one side of the band and filled with air to compress a skin surface of a wrist; and a pressure sensor which is provided to measure blood pressure from an aorta radialis when the air chamber is compressed for pressing the aorta radialis.

The band may include a single-body elastic band which has elasticity and of which diameter can be enlarged by external force.

Further, the air chamber may be made of silicon, urethane or rubber.

The pressure sensor may be provided at a side of the measured blood pressure display, and be connected to the air chamber by an air hose through which change in pressure is transferred to the pressure sensor.

The pressure sensor may be provided inside the air chamber, and an input value detected by the pressure sensor may be transmitted to the measured blood pressure display through a signal line.

The air chamber may further include an air inlet to adjust pressure of air injected therein.

The wrist watch style blood pressure monitor may further include a wireless communication unit to send a value of the measured blood pressure to a set Smartphone.

Advantageous Effects

According to an embodiment of the present invention, the wrist watch style blood pressure monitor has the following effects.

First, according to an embodiment of the present invention, the blood pressure monitor is wearable at ordinary times like a wrist watch, is convenient to measure the blood pressure as necessary, and is capable of accurately measuring the blood pressure even though it has a simple structure without a separate pump.

According to an embodiment of the present invention, there is provided the blood pressure measuring device, which is convenient for an examinee to measure the blood pressure since it does not interfere with behavior of an examinee who has to periodically check his/her blood pressure.

Further, it is important to measure and record blood pressure at the same time every day in order to determine a pattern of changing blood pressure. According to an embodiment of the present embodiment, the wrist watch style blood pressure monitor is very useful to measure blood pressure of the examinee at the same time every day since it is provided in the form of a wrist watch style and wearable at ordinary times, and is very advantageous to regularly measure the blood pressure without omissions if an alarm is given.

According to an embodiment of the present invention, the data of the measured blood pressure is sent to an attending physician or a medical specialist through a wireless communication unit and then analyzed, so that it can be more effective to patients with high blood pressure, diabetes, hepatic impairment, hardening of arteries, peripheral nerve disorder of blood circulation, etc.

According to an embodiment of the present invention, if the air chamber further includes an air inlet, it is more effective to control measurement sensitivity of the blood pressure monitor by adjusting pressure of air injected therein.

DESCRIPTION OF DRAWINGS

The above and/or other aspects will become apparent and more readily appreciated from the following description of exemplary embodiments, taken in conjunction with the accompanying drawings, in which:

FIG. 1 is a cross-section view of a wrist watch style blood pressure monitor according to an embodiment of the present invention;

FIG. 2 is a development view for explaining elements of the wrist watch style blood pressure monitor shown in FIG. 1;

FIG. 3 is a cross-section view of a wrist watch style blood pressure monitor according to another embodiment of the present invention;

FIG. 4 is a development view for explaining elements of the wrist watch style blood pressure monitor shown in FIG. 3;

FIG. 5 is a block diagram of the wrist watch style blood pressure monitor according to the present invention.

BEST MODE

Hereinafter, exemplary embodiments of the present invention will be described in detail with reference to the accompanying drawings, FIGS. 1 to 5. Like reference numerals in the drawings denote like elements throughout.

Embodiment 1

First, referring to FIG. 1 and FIG. 2, a wrist watch style blood pressure monitor 1 according to this embodiment is a blood pressure monitor that can be mounted to a wrist of an examinee at ordinary times. The wrist watch style blood pressure monitor 1 includes a blood pressure monitor main body 100 with a measured blood pressure display 101 for displaying measured blood pressure of an examinee, a band 110 coupled to the measured blood pressure display 101 and wound around a wrist, an air chamber 120 provided at one side of the band 110 and filled with air to press a skin surface of the wrist, and a pressure sensor 130 provided to measure blood pressure from an aorta radialis when the air chamber 120 is compressed.

The pressure sensor 130 is provided at a side of the measured blood pressure display 101, and connected to the air chamber 120 by an air hose 140 through which change in pressure can be transferred to the pressure sensor 130.

The air chamber 120 may be made of silicon, urethane or rubber, but not limited thereto. Alternatively, the air chamber may be made of any material that can be expanded and contracted.

In this embodiment, the air chamber 120 is enclosed so that air previously injected therein to keep a predetermined pressure cannot be added with more air or exhausted.

The band 110 is divided into a left band portion and a right band portion, and the ends of the left band portion and the right band portion are provided with fastening portions 131 so as to couple both ends of the left band portion and the right band portion.

The fastening portion 131 may be achieved by various types such as a Velcro type, a hook type, etc.

With this configuration, operations of the wrist watch style blood pressure monitor 1 according to an embodiment of the present invention will be described below.

Using the wrist watch style blood pressure monitor 1 according to this embodiment, the blood pressure is measured as follows. While the air chamber 120 positioned corresponding to a part of the wrist where the aorta radialis passes is compressed enough to stop flow of blood in the aorta radialis and then decompressed at a constant speed, the pressure sensor 130 senses pulse waves, thereby measuring systolic pressure and diastolic pressure.

Pressure that has a constant level as compared with the maximum amplitude of the pulse wave may be taken as the systolic pressure or the diastolic pressure, or pressure of when the pulse wave amplitude is rapidly changed may be taken as the systolic pressure or the diastolic pressure. During the decompression at a constant speed after the compression, the systolic pressure is measured earlier than the moment when the pulse wave has the maximum amplitude and the diastolic pressure is measured later than the moment when the pulse wave has the maximum amplitude.

It is important to measure and record blood pressure at the same time every day in order to determine a pattern of changing blood pressure. According to the present embodiment, the wrist watch style blood pressure monitor 1 is very useful for an examinee or his/her guardian to measure blood pressure of the examinee at the same time every day since it is provided in the form of a wrist watch style and wearable at ordinary times.

In other words, the wrist watch style blood pressure monitor 1 according to this embodiment is very helpful to manage the blood pressure since it can be worn at ordinary times like a wrist watch and regularly take the blood pressure.

On the contrary to the existing blood pressure monitor, the wrist watch style blood pressure monitor 1 according to this embodiment is capable of accurately measuring the blood pressure even though it has a simple structure without a cuff, a pump or the like.

The wrist watch style blood pressure monitor according to an embodiment of the present invention may have an alarm function and/or a watch function to be described in the following embodiment 2. However, it will be appreciated that the present invention includes a blood pressure monitor with a structure to be mounted to a wrist just like a wrist watch without a built-in watch.

Embodiment 2

FIG. 3 is a cross-section view of a wrist watch style blood pressure monitor according to another embodiment of the present invention, and FIG. 4 is a development view for explaining elements of the wrist watch style blood pressure monitor shown in FIG. 3.

Referring to FIG. 3 and FIG. 4, a wrist watch style blood pressure monitor 1 according to this embodiment has the same configurations as those of the foregoing [Embodiment 1] except the following configurations.

The wrist watch style blood pressure monitor 1 according to this embodiment further includes a wireless communication unit 150 such as BLUETOOTH™ or the like for transmitting data of the measured blood pressure to a preset mobile phone, for example, a smart phone.

The wireless communication unit 150 may be configured to transmit a distress signal under a certain situation, for example an emergency situation to an external communication device as well as the data of the measured blood pressure.

Further, a watch with an alarm function, in particular an electronic watch may be further provided to measure and record the blood pressure at exactly the same time every day. The watch may be arranged together with or neighboring with the measured blood pressure display 101 that displays the measured blood pressure of an examinee, but not limited thereto.

As compared with the foregoing embodiment where the air chamber 120 is enclosed, this embodiment further includes an air inlet 121 provided at a side of the air chamber 120 and adjusting pressure of air injected therein so that measurement sensitivity of the blood pressure monitor can be controlled. Of course, air may be injected into the air chamber 120 through the air inlet 121 by a portable air pump or a syringe as if air is generally pumped into a soccer ball.

With this configuration, operations of the wrist watch style blood pressure monitor 1 according to the present embodiment will be described below.

Using the wrist watch style blood pressure monitor 1 according to this embodiment, the blood pressure is measured by the foregoing [Embodiment 1].

That is, while the air chamber 120 positioned corresponding to a part of the wrist where the aorta radialis passes is compressed enough to stop flow of blood in the aorta radialis and then decompressed at a constant speed, pulse waves are sensed, thereby measuring systolic pressure and diastolic pressure.

Instead, the wrist watch style blood pressure monitor 1 in this embodiment is different from that of the [Embodiment 1] as follows in light of operations before and after measuring the blood pressure.

First, it is important to measure and record blood pressure at the same time every day in order to determine a pattern of always changing blood pressure. According to the present embodiment, the blood pressure monitor according to this embodiment is very useful to measure blood pressure at the same time every day since it is provided in the form of a wrist watch style and wearable at ordinary times.

Further, the blood pressure monitor in this embodiment has an alarm function for giving an alarm at a set time to measure the blood pressure, thereby very efficiently and regularly measuring and managing the blood pressure since the blood pressure is easily measured and recorded at the same time every day.

In particular, according to this embodiment, the wireless communication unit 150 such as a BLUETOOTH™ is further provided to send the data of the measured blood pressure to a set Smartphone, so that the data of the measured blood pressure can be sent in real time to an attending physician or a medical specialist through the Smartphone and then analyzed That is, more care is needed for persons with high blood pressure, diabetes, hepatic impairment, hardening of arteries, peripheral nerve disorder of blood circulation, etc., and thus the blood pressure monitor in this embodiment is particularly efficient to manage the blood pressure of such patients since it has a function of transmitting data.

Referring to FIG. 5, the blood pressure monitor main body 100 of the wrist watch style blood pressure monitor 1 may further include a data storage unit 160 for storing data measured in a blood pressure measurer 161 for measuring the blood pressure, a display unit 170 for display an image based on the measured data, time and other pieces of information, a user registration unit 180 for managing a user's measurement history and a user's identification (ID), and a control unit 190 for collecting and analyzing data and controlling a designated distress signal to be transmitted when a user is in an emergency situation in addition to the wireless communication unit 150 of transmitting the measured data selected by a user and the distress signal to the external communication device.

Although a few exemplary embodiments of the present invention have been shown and described, it will be appreciated by those skilled in the art that changes may be made in these embodiments without departing from the principles and spirit of the invention For example, on the contrary to the foregoing embodiments, the band 110 may be achieved by a single-body elastic band which has elasticity without the separate fastening portion and of which diameter can be enlarged by external force. That is, the band 110 may be a solid body without being divided into the left band portion and the right band portion.

Further, on the contrary to the foregoing embodiments where the pressure sensor 130 is connected by the air hose 140, the pressure sensor 130 may be provided inside the air chamber 120, and an input value detected by the pressure sensor 130 may be transmitted to the measured blood pressure display 101 through a separate electric signal line.

Some elements proposed in [Embodiment 2], for example, the electronic watch with the alarm function or the wireless communication unit may be added or combined to the elements of [Embodiment 1].

Therefore, the foregoing embodiments are provided for illustrative purposes only and are not intended to limit the scope of the invention, and therefore changes may be made in these embodiments without departing from the principles and spirit of the invention, the scope of which is defined in the appended claims and their equivalents.

INDUSTRIAL APPLICABILITY

The present invention provides a wrist watch style blood pressure monitor, which is portable being mounted to a wrist of an examinee and measures blood pressure. The wrist watch style blood pressure monitor can be widely used in field of medical devices, be wearable at ordinary times like a wrist watch, be convenient to measure the blood pressure as necessary, and be capable of accurately measuring the blood pressure even though it has a simple structure without a separate pump.

What is claimed is:

1. A wrist watch style blood pressure monitor, comprising:
   a main body which comprises a display to indicate a blood pressure of an examinee;
   a band which is coupled to the main body and wound around a wrist of the examinee;
   an air chamber which is provided at one side of the band and filled with air with a predetermined pressure to compress a skin surface of the wrist; and
   a pressure sensor which is provided to measure a blood pressure from an aorta radialis based on a pressure change in the air chamber when the air chamber compresses the aorta radialis,
   wherein the air chamber has no inlet through which air is injected into the air chamber from an outside of the wrist style blood pressure monitor, and is hermetic such that no air flows into and out from the air chamber, and
   wherein the air chamber is manually compressed and then manually decompressed such that the pressure sensor senses pulse waves of the examinee.

2. The wrist watch style blood pressure monitor according to claim 1, wherein the band comprises a single-body elastic band which has elasticity and of which diameter can be enlarged by external force.

3. The wrist watch style blood pressure monitor according to claim 1, wherein the air chamber comprises silicon, urethane or rubber.

4. The wrist watch style blood pressure monitor according to claim 1, wherein the pressure sensor is provided at a side of the display, and is connected to the air chamber by an air hose through which the pressure change in the air chamber is transferred to the pressure sensor.

5. The wrist watch style blood pressure monitor according to claim 1, wherein the pressure sensor is provided inside the air chamber, and an input value detected by the pressure sensor is transmitted to the display through a signal line.

6. The wrist watch style blood pressure monitor according to claim 1, further comprising a wireless communication unit to send a value of the measured blood pressure to a set Smartphone.

7. The wrist watch style blood pressure monitor according to claim 2, further comprising a wireless communication unit to send a value of the measured blood pressure to a set Smartphone.

8. The wrist watch style blood pressure monitor according to claim 3, further comprising a wireless communication unit to send a value of the measured blood pressure to a set Smartphone.

9. The wrist watch style blood pressure monitor according to claim 4, further comprising a wireless communication unit to send a value of the measured blood pressure to a set Smartphone.

10. The wrist watch style blood pressure monitor according to claim 5, further comprising a wireless communication unit to send a value of the measured blood pressure to a set Smartphone.

11. The wrist watch style blood pressure monitor according to claim 1, further comprising a watch unit configured to provide an alarm message at a predetermined time to monitor and measure the blood pressure regularly.

\* \* \* \* \*